United States Patent [19]

Bambeck et al.

[11] Patent Number: 4,909,918
[45] Date of Patent: Mar. 20, 1990

[54] DISPOSABLE COMB FOR ELECTROPHORESIS DEVICE

[76] Inventors: Gregory S. Bambeck, 2708 St. Elmo Ave., Canton, Ohio 44714; Kenneth R. Sibley, 2408 Benton St., Akron, Ohio 44312

[21] Appl. No.: 240,540
[22] Filed: Sep. 6, 1988
[51] Int. Cl.⁴ .............................................. G01N 27/26
[52] U.S. Cl. ............................. 204/299 R; 204/152.8
[58] Field of Search ......................... 204/299 R, 182.8

[56] References Cited

U.S. PATENT DOCUMENTS

| | | | |
|---|---|---|---|
| 3,616,387 | 10/1971 | Siebert et al. | 204/299 R X |
| 4,035,377 | 7/1977 | Detroy | 204/299 R |
| 4,325,796 | 4/1982 | Hoefer et al. | 204/299 R X |
| 4,431,506 | 2/1984 | Gorman, Jr. et al. | 204/299 R |
| 4,762,743 | 8/1988 | von Alven et al. | 204/182.8 X |

*Primary Examiner*—John F. Niebling
*Assistant Examiner*—John S. Starsiak, Jr.
*Attorney, Agent, or Firm*—Oldham & Oldham

[57] ABSTRACT

A disposable comb for a vertical gel cassette of a vertical electrophoresis device is disclosed. The comb is formed from a single thin sheet of a plastic, preferrably biaxial polystyrene, which has at least a slight degree of resilience. A comb is rectangular in shape, and has a plurality of equally spaced parallel ridges or ribs which extend from one side of the sheet to the other (from top to bottom as the comb is inserted into a vertical gel cassette). The comb has a plurality of relatively wide coplanar flat portions alternating with relatively narrow parallel ridges, which resemble the teeth of a comb. The tops of the ridges are slightly convex. The disposable comb is placed into a vertical gel cassette comprising a pair of closely spaced walls, so that the coplanar flat portions of a comb engaged inside surface of one wall while the ridges engage in the inside of the surface of relatively wide spaced paralleled sample wells which are adapted to receive a mixture of macromolecules which are to be separated, alternating with realtively narrow spacer channels.

5 Claims, 2 Drawing Sheets

DISPOSABLE COMB FOR ELECTROPHORESIS DEVICE

TECHNICAL FIELD

This invention relates to electrophoresis apparatus and particularly to vertical electrophoresis devices and components therefor. More particularly, this invention relates to a disposable comb which is useful in forming sample lanes in a vertical electrophoresis device.

BACKGROUND ART

Elecrophoresis involves the separation of charged macromolecular species in a carrier medium in an electric field. Now electrophoresis involves migration of those charged molecular species through a porous gel under an applied electric field. Most widely used gel is polyacrylamide, typically cross linked with a small amount of bis-acrylamide; however, other gels may also be used.

Gel electrophoresis separations may be on the basis of molecular weight, pH or a combination of the two. Suitable gels and techniques for each type of separation are known. Electrophoresis separation is more widely used for separation of mixture of macromolecules according to molecular weight.

Electrophoresis is a particularly desirable tool for separation or fractionation of macromolecular mixtures in which the molecular weights of the species present are from about 10,000 to about 1 million. Gel electrophoresis is a particularly suitable technique for fractionating protein mixtures, including gene mixtures used in genetic studies.

While electrophoresis has some limited use as a preparative tool, it is more widely used as an analytical tool.

Gel electrophoresis apparatus may be classified into two general types: vertical and horizontal. Both types have been extensively described in the literature including patents. Vertical electrophoresis devices have an advantage in that cleaner separations and smoother flow of the macromolecular mixture to be fractionated are generally possible in vertical apparatus than in horizontal apparatus.

U.S. Pat. No. 4,707,233 shows a representative vertical gel electrophoresis device. The apparatus shown therein comprises an open top container or tank having a basket-like gel slab holder which is placed within the container or tank, a vertical gel slab (or gel cassette) extending through the bottom wall of the gel slab holder, a gasket forming a fluid tight joint between the gel slab and the gel slab holder, and oppositely charged electrodes on opposite sides of the gel slab holder walls, so that electric current must pass through the gel slab. The gel slab comprises pair of parallel plates joined together along their vertical edges by spacers, so that the gel slab is open at the top and bottom but not along the sides, and a sample holder resembling a comb for directing a macromolecular mixture through the gel slab. The comb has a plurality of dividers forming side by side sample wells. This electrophoresis device is not disclosed as being capable of fractionating more than one macromolecular mixture at a time, and would not be suitable for simultaneous resolution of multiple mixtures. The thickness of the dividers in the comb would then cause an uneven electric flux density in the electrical field within the gel slab, with the result that macromolecule streams descending from the sample holder would tend to merge and thus make simultaneous multiple fractionations impossible.

A reusable comb providing a plurality of sample wells and making simultaneous multiple separations possible was developed several years ago by one of the inventors herein and is shown in FIG. 1. FIG. 1 is a top view of this prior art comb. Referring now to FIG. 1, this reusable prior art comb 10 comprises a thin opaque (preferably white) rectangular horizontally extending plastic sheet 12 which is flat before forming, and which as formed comprises a plurality of relatively wide coplanar flat portions 13 alternating with relatively narrow ridges or ribs 14 of square tooth configuration. These ribs 14 extend transversely the entire width of the plastic sheet 12, i.e., from top to bottom. The plastic sheet has two shorter sides of the rectangle. Plastic sheet 12 is laminated to a facing sheet 18 and backing sheet 20, both of which are thin essentially flat transparent rectangular plastic sheets, thinner than sheet 12. The flat main portions 13 of plastic sheet 12 are laminated to the backing sheets 20 while the peaks of ridges 14 are laminated to the facing sheet 18. For the most part facing sheet 18 and backing sheet 20 are parallel and are spaced apart by the height of ridges 14 in plastic sheet 12. However, facing sheet 18 and backing sheet 20 are joined together along parallel side edges 22 thereof, laterally outwardly from the end portions of 16 of plastic sheet 12. This structure forms a plurality of relatively wide vertically extending sample wells, 24, alternating with spacer channels 26 which are much narrower. Sample wells 24 and spacer channels 26 are opened at the top and bottom.

Reusable comb 10 is placed inside a vertical gel cassette 28, shown in broken lines, which is a rectangular prism having a pair of spaced parallel plates forming side walls, and a pair of end walls, providing a vertically extending central opening 30 of rectangular cross section and of width much greater than its thickness. Central opening 30 is open at its top and bottom but is closed along its sides.

The entire interior space 30 of gel cassette 28, including sample wells 24 and spacer channels 26, is filled with a suitable electrophoresis gel e.g., polyacrylamide of gradient concentration, cross linked with a small amount of bis-acrylamide, to achieve the desired fractionation according to molecular weight and/or charge.

Representative dimensions of reusable comb 10 are as follows: width, 16 cm; height (perpendicular to the plane of the paper in FIG. 1), 7 cm; thickness, about 1.5 mm. Representative sheet thicknesses are as follows: opaque plastic sheet 12, 0.2 mm; facing sheet 18 and backing sheet 20, each 0.2 mm. These dimensions may vary, as the thickness of gel cassette 28 and comb 10 are about equal, the former being just enough thicker as to permit insertion and removal of the comb while holding it in place.

A major advantage of the comb 10 over previously known combs or arrangements for vertical electrophoresis devices is that the comb 10 permits simultaneous multiple channel separation of macromolecule mixtures. Separate mixtures may be charged to each of the sample wells 24, and the respective mixtures remain in seperate and distinct lanes are achieved because the electric flux is substantially uniform over the entire interior space 30 of the gel cassette when a comb such as comb 10 illustrated in FIG. 1 is used. The disadvantage of comb 10 is that it is costly to assemble. Lamination of plastic sheet 12 to facing and backing sheets 18 and 20, respectively, must be done by hand, and therefore is the major cost factor. As a result of this high cost combs 10 must be reused. While they are durble and can be used through a number of cycles, they must be cleaned after each cycle, which is difficult because of the small dimensions involved.

DISCLOSURE OF THE INVENTION

The present invention provides a disposable one piece comb for a gel electrophoresis device of the type of which has a gel cassette comprising a pair of closely spaced parallel plates providing space for a gel therebetween. The comb of this invention consists essentially of a single thin rectangular sheet having a plurality of spaced parallel ridges and a plurality of spaced coplanar flat portions extending between two opposites sides of said sheet, the flat portions being substantially wider than the ridges, said ridges being of substantially uniform height as measured from the plane of the flat portions. Preferably the central portions or the tops of the ridges are slightly domed (i.e., convex), and the plastic sheet material has at least a slight degree of resilience. The disposable comb is adapted to inserted into a vertical gel cassette, such as that shown in FIG. 1, so that the coplanar flat protions engage one wall of the cassette and the ridges engage the opposite wall. This provides alternating sample wells and spacer channels similar to those shown in FIG. 1. The domed ridges and the slight resilience of the plastic sheet material achieve greater fluid tightness than would be the case otherwise.

The disposable comb of this invention is simple, can be made of a fraction of cost of the prior art reusable comb shown in FIG. 1, and achieve just as good results in practice.

BEST MODE FOR CARRYING OUT THE INVENTION

The preferred embodiment of this invention will now be described in detail with reference to FIGS. 2 to 6 of the drawings.

Figure 2:
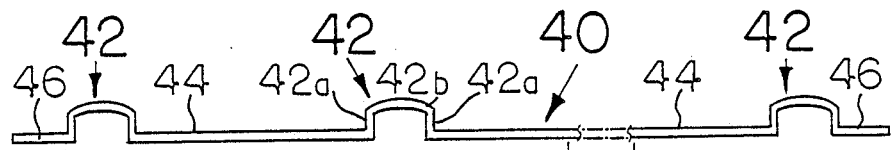
FIG. 2 is a top view of a disposable comb according to preferred embodiment of this invention.
Figure 3:
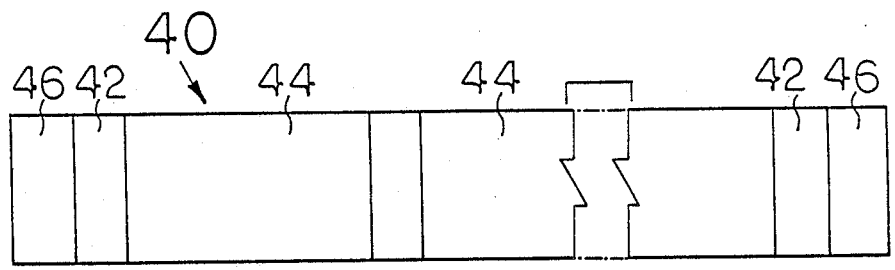
FIG. 3 is a front view of the preferred disposable comb of this invention.

Referring now to FIGS. 2 and 3, 40 is a disposable comb according to the preferred embodiment of this invention. Disposable comb 40 is formed from a single flat rectangular plastic sheet, preferably white opaque, and comprises a plurality of equally spaced comparatively narrow hollow parallel transversely extending ridges or ribs 42, which extend from one side of the sheet to the other may be seen in FIG. 3, alternating with coplanar flat portions 44 which are much wider than the ridges 42. Ridges 42 resemble the teeth of a comb in appearance. Each ridge 42 has two parallel sidewalls 42a and a domed central portion 42b. At either end of the comb are flat end portions 46 which are coplanar with flat portions 44. The outer surfaces of the domed central portions 42b of ridges 42 are preferably slightly convex (preferably cylindrical in curvature) as shown rather than being flat, in order to give better adhesion of the comb to a gel cassette wall as will be hereinafter discussed. Also for better adhesion, the plastic material of which comb 40 is made has at least a slight degree of resilience. A particularly preferred comb 40 of this invention has an overall length of 74 mm (as shown from left to right in FIGS. 2 and 3), an overall height of 15 mm (as seen in FIG. 3), an overall thickness (which is the height of ridges 42 above the plane of flat portions 44, as may be seen in FIG. 2) of about 1.1. mm. Thermoformed biaxial white opaque polystyrene is the preferred material. The preferred thickness of the polystyrene is about 7 mils (0.007 inch or about 0.018 mm. Each ridge 42 is preferably 2 mm wide and each flat portion 44 is preferable 8 mm wide. The ridge side walls 42a are about 1.0 mm high, and the height of domed central portions 42b (measured from the plane of flat portions 44 to the longitudinal centerline of a domed portion 42b) is about 1.1 mm. in this preferred embodiment. These dimensions are merely exemplary and can be modified. However, the overall sheet thickness of comb 40 should not be substantially in excess of about 0.010 inch (approximately 0.25 mm) since any given material tends to lose some of its resilience as it is increases in thickness, nor less than about 0.002 inch for structural reasons. Also, for preferred electrical characteristics and channel separation of samples being fractionated (to be discussed in greater detail hereinafter), the width ratio of ribs 42 to flat portions 44 should not be greater than about 1:3 nor less than about 1:10 in order to insure good electrical characteristics and good lane or channel separation.

Figure 4:
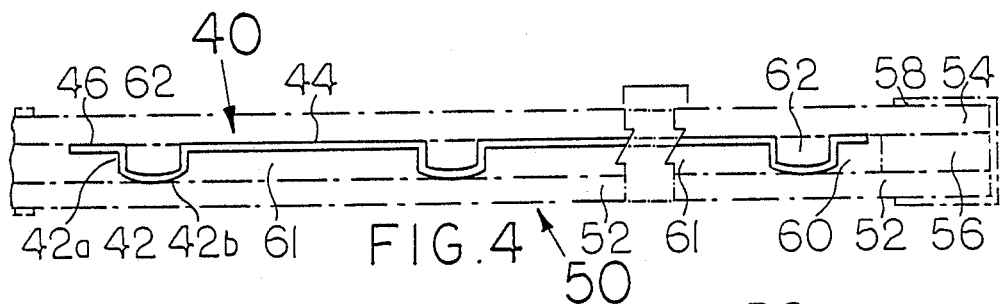
FIG. 4 is a top view of an assembly of the preferred disposable comb of this invention in a vertical gel cassette, wherein the gel cassette is shown in phantom lines.
Figure 5:
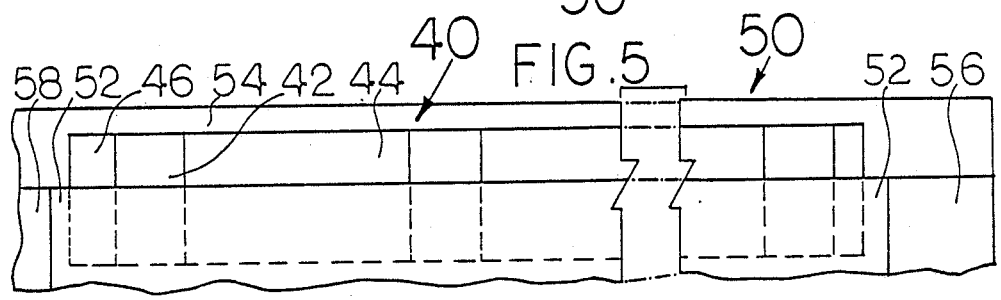
FIG. 5 is a front view of an assembly of the preferred disposable comb of this invention in a vertical gel cassette.
Figure 6:
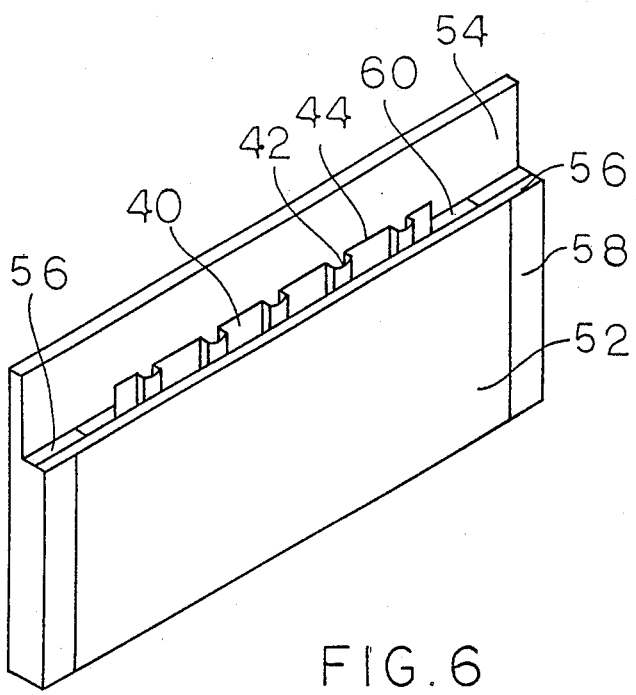
FIG. 6 is an isometric view of an assembly of the preferred disposable comb of this invention in a gel cassette.

An assembly of a comb 40 of this invention in a gel cassette 50 will now be described with reference to FIGS. 4–6. Referring now to FIGS. 4–6, vertical gel cassette 50, which may be of a type known in the art, is a thin hollow rectangular solid comprising a pair of spaced parallel plates, i.e., facing plate 52 and a backing plate 54, which are spaced apart the desired distance by vertical spacers 56 which extends along two opposite sides of plates 52 and 54. The assembly of plates 52, 54 and spacer 56 is held together by suitable means, e.g. by strips of adhesive tape 58 which overlie the exteriors of spacers 56 and the adjacent portions of plates 52 and 54. Plates 52 and 54 are preferably transparent and may be either glass or transparent plastic. Preferably backing plate 54 is slightly higher than (but of the same width as) facing plate 52. Plates 52 and 54 and spacers 56 surround an interior space 60 which is open at the top and bottom for charging and discharging, respectively, samples being analyzed.

The hollow interior space 60 of cassette 50 is filled with electrophoresis gel. Any of the electrophoresis gels is known in the art may be used. For instance, a polyacryalmide gel, which may be cross linked with a small amount of cross linking agent (e.g., bis-acrylamide) and which may have a gradient concentration (more concentrated at the bottom of the cassette than at the top) may be used for separation of macromolecular species and particularly proteins wherein the minimum molecular weight present is about 10,000 or higher.

As may be seen in FIGS. 5 and 6, comb 40 is inserted into the top opening of the interior space of cassette 50, so that the comb is partially above and partially below the top edge of the facing plate 52. The top edge of the comb 40 is below the top edge of the backing plate 54. It is not necessary for comb 40 to be as quite long as the width of interior space of cassette 50, as may be appreciated from FIGS. 4-6. Comb 40 is constructed so that the comparatively wide flat portions 44 are in frictional engagement with the inside surface of backing plate 54, while the peaks of ridges 42 are in frictional engagement with the inside surfaces of the facing plate 52. Preferably the distance from the plane of wide portions 44 to the peaks of ridges 42 is just slightly greater than the thickness of the interior space 60 of the cassette, so that the domed portions of the ridges 42 will be slightly flattened. This assures that the ridges 42 will make a fluid tight contact with the cassette wall. In a preferred embodiment the thickness of interior space 60 is about 1.0 mm., and as proviously explained the distance from the plane of wide portions 44 to the peaks of ridges 42 (i.e. the centerlines of domed portions 42b) is about 1.1 mm.

Comb 40 forms with the cassette wall alternating comparatively wide sample wells 61 and comparatively narrow spacer channels 62, as is best seen in FIG. 4. Sample well 61 and spacer channels 62 are open at the top and bottom.

In operation, macromolecule mixtures to be fractionated are charged to the top of sample wells 61. Samples may be charged in a conventional manner. Charging is facilitated by the fact that backing plate 54 is higher than facing plate 52 and comb 40 projects above the top edge of facing plate 52. The number of samples which can be fractionated simultaneously is equal to the number of sample wells in comb 40. For example, a comb having a specific dimensions given above by way of example as seven sample wells. An electric field (e.g., mean value 155 volts DC, which may be pulsed), is applied across the gel cassette in a conventional manner. The macromolecule mixtures charged to sample well 61 descend in distinct parallel lanes through the gel in the cassette 50 below the sample wells. When a gel such as acrylamide is used, molecular species are fractionated in accordance with molecular weight, the lowest molecular weight species descending the farthest, as is well known. Comb 40 of this invention may also be used in electrophoresis process wherein mixtures are resolved and the species having different isoelectric points, by appropriate choice of electrophoresis gel.

The unique design of the comb of this invention results in a substantially uniform electric field over the entire width of the gel cassette 50, including the portion thereof containing comb 40 and the portion thereof below comb 40. This electric field embraces the gel contained in spacer channels 62, and the gel which is below the comb 40 entirely. This substantially uniform electric field is achieved because the sheet thickness of comb 40 is quite small even compared to the width of spacer channel 62. Because of this iniform electric field plus the fact that spacer channels 62 are at least as 1/10 as wide (and in the preferred embodiment ¼ as wide) as the sample well 61, one achieves distinct parallel lanes of samples throughout the gel cassette.

Figure 1:
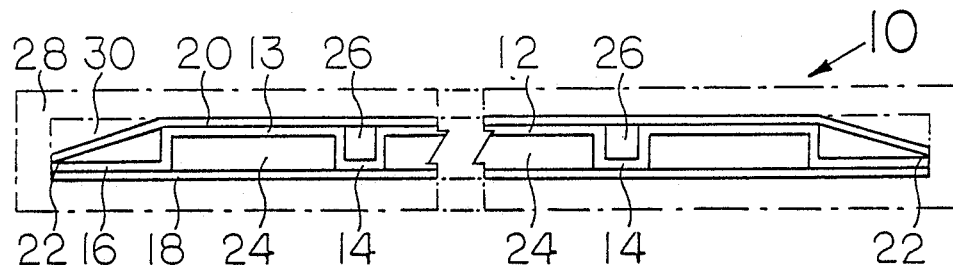
FIG. 1 is a top view of a prior art reusable comb.

The comb on the present invention, when inserted into a vertical gel cassette as described, is highly reliable in operation. Furthermore, this comb is very simple, constituting only one piece, and is inexpensive to manufacture. As a result of its low cost, it may be discarded after a single use, greatly simplifying cleanup of the apparatus as opposed to the cleanup operation required when a reusable comb (such as that illustrated in FIG. 1) or a comb which is a permanent part of the cassette, is used.

While in accordance with the patent statutes only the best mode and preferred embodiment of the invention has been illustrated and described in detail, it is to be understood that the invention is not limited thereto or thereby, but that the scope of the invention is defined by the appended claims.

What is claimed is:

1. A disposable one-piece comb for a gel electrophoresis device having therein a gel a cassette comprising a pair of closely spaced parallel plates providing space for a gel therebetween, said comb being formed from a single thin rectangular sheet and having a plurality of spaced hollow parallel ridges and a plurality of spaced parallel coplanar flat portions therebetween, said ridges and said flat portions extending between opposite side of said sheet said ridges having convex central portions and being of substantially uniform height as measured from the plane of said flat portions; said comb being adapted to be inserted into said cassette so that the flat portions are in frictional engagement with one of said parallel plates, and the ridges are in frictional engagement with the other of said parallel plates, whereby said comb and said parallel plates together form a plurality of parallel sample wells for gel and material to be fractionated in alternating relationship with parallel spacer channels for gel alone.

2. A disposable comb according to claim 1 in which each ridge comprises a pair of side walls which are perpendicular to the plane of said flat portions, and a domed central portion.

3. A disposable comb according to claim 1 in which said comb is made of a plastic sheet material having at least a slight degree of resilience.

4. A disposable comb according to claim 1 in which said ridges are of substantially equal width, said rigdes being approximately 1/10 to approximately ⅓ as wide as said flat portions.

5. A disposable comb according to claim 1 in which said wells are substantially wider than said spacer channels.

* * * * *